United States Patent
Wagner et al.

(10) Patent No.: US 11,590,162 B2
(45) Date of Patent: Feb. 28, 2023

(54) BIODEGRADABLE, ANTIOXIDANT, THERMALLY RESPONSIVE INJECTABLE HYDROGEL AND USES THEREFOR

(71) Applicant: University of Pittsburgh—Of the Commonwealth System of Higher Education, Pittsburgh, PA (US)

(72) Inventors: William R. Wagner, Gibsonia, PA (US); Yasumoto Matsumura, Pittsburgh, PA (US); Murugesan Velayutham, Pittsburgh, PA (US); Yang Zhu, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 51 days.

(21) Appl. No.: 16/336,994

(22) PCT Filed: Oct. 6, 2017

(86) PCT No.: PCT/US2017/055564
§ 371 (c)(1),
(2) Date: Mar. 27, 2019

(87) PCT Pub. No.: WO2018/067948
PCT Pub. Date: Apr. 12, 2018

(65) Prior Publication Data
US 2019/0216847 A1    Jul. 18, 2019

Related U.S. Application Data

(60) Provisional application No. 62/405,441, filed on Oct. 7, 2016.

(51) Int. Cl.
| | | |
|---|---|---|
| A61K 31/74 | (2006.01) | |
| A61K 31/79 | (2006.01) | |
| A61K 9/00 | (2006.01) | |
| C08F 290/06 | (2006.01) | |
| A61L 31/14 | (2006.01) | |
| C08F 220/54 | (2006.01) | |
| C08F 299/04 | (2006.01) | |

(52) U.S. Cl.
CPC ............ *A61K 31/79* (2013.01); *A61K 9/0019* (2013.01); *A61K 9/0024* (2013.01); *A61L 31/145* (2013.01); *C08F 220/54* (2013.01); *C08F 290/061* (2013.01); *C08F 299/045* (2013.01); *A61L 2400/06* (2013.01); *C08F 2438/02* (2013.01)

(58) Field of Classification Search
None
See application file for complete search history.

(56) References Cited

U.S. PATENT DOCUMENTS

| | | |
|---|---|---|
| 5,763,548 A | 6/1998 | Matyjaszewski et al. |
| 5,789,487 A | 8/1998 | Matyjaszewski et al. |
| 5,807,937 A | 9/1998 | Matyjaszewski et al. |
| 6,541,580 B1 | 4/2003 | Matyjaszewski et al. |
| 7,678,869 B2 | 3/2010 | Matyjaszewski et al. |
| 8,461,132 B2 | 6/2013 | Cohen et al. |
| 8,673,295 B2 | 3/2014 | Fujimoto et al. |
| 8,889,791 B2 | 11/2014 | Guan et al. |
| 9,005,672 B2 | 4/2015 | Michal et al. |
| 9,968,681 B2 | 5/2018 | Weiss et al. |
| 2003/0120028 A1 | 6/2003 | Lin et al. |
| 2005/0154376 A1 | 7/2005 | Riviere et al. |
| 2010/0196481 A1 | 8/2010 | Pritchard et al. |
| 2011/0117195 A1 | 5/2011 | Hsieh et al. |
| 2017/0028101 A1 | 2/2017 | Jiang et al. |

FOREIGN PATENT DOCUMENTS

| | | |
|---|---|---|
| CN | 101574514 A | 11/2009 |
| CN | 101618235 A | 1/2010 |
| EP | 2109469 B1 | 6/2014 |
| WO | 02087481 A1 | 11/2002 |
| WO | 2008045904 A2 | 4/2008 |
| WO | 2010036961 A1 | 4/2010 |
| WO | 2010127254 A2 | 11/2010 |
| WO | 2010147632 A1 | 12/2010 |
| WO | 2012164101 A1 | 12/2012 |
| WO | 2015160793 A1 | 10/2015 |
| WO | WO 2015/160793 | * 10/2015 |

OTHER PUBLICATIONS

Uemukai et al. (International Journal of Polymer Science vol. 2013, 1-9) Thermoresponsive and Redox Behaviors of Poly(N-isopropylacrylamide)-Based Block Copolymers Having TEMPO Groups as Their Side Chains.*

Zhou et al. (Current Organic Chemistry, 2014, 18, 459-474). TEMPO and its Derivatives: Synthesis and Applications.*

Chou et al., "Gallic acid grafting effect on delivery performance and antiglaucoma efficacy of antioxidant-functionalized intracameral pilocarpine carriers", Acta Biomaterialia, 2016, pp. 116-128, vol. 38.

Cui et al., "In Vitro Study of Electroactive Tetraaniline-Containing Thermosensitive Hydrogels for Cardiac Tissue Engineering", Biomacromolecules, 2014, pp. 1115-1123, vol. 15, No. 4.

Li et al., "Injectable, Highly Flexible, and Thermosensitive Hydrogels Capable of Delivering Superoxide Dismutase", Biomacromolecules, 2009, pp. 3306-3316, vol. 10, No. 12.

Ma et al., "A thermally responsive injectable hydrogel incorporating methacrylate-polyactide for hydrolytic lability", Biomacromolecules, 2010, pp. 1873-1881, vol. 11, No. 7.

(Continued)

*Primary Examiner* — Tigabu Kassa
(74) *Attorney, Agent, or Firm* — The Webb Law Firm

(57) ABSTRACT

Provided herein are antioxidant, thermally-responsive copolymer-based compositions and methods of making and using the compositions, e.g., for treatment of ischemia reperfusion injury in a patient. The copolymer comprises a hydrocarbyl backbone, and a plurality of pendant pyrrolidone, antioxidant radical, polyester oligomer, and N-alkyl amide groups.

3 Claims, 6 Drawing Sheets

(56) References Cited

OTHER PUBLICATIONS

Nelson et al., "Intramyocardial Biomaterial Injection Therapy in the Treatment of Heart Failure: Materials, Outcomes and Challenges", Acta Biomaterialia, 2011pp. 1-15, vol. 7, No. 1.
Pua et al., "Redox-active injectable gel using thermo-responsive nanoscale polyion complex flower micelle for noninvasive treatment of local inflammation", Journal of Controlled Release, 2013, pp. 914-920, vol. 172, No. 3.
Seif-Naraghi et al., "Safety and efficacy of an injectable extracellular matrix hydrogel for treating myocardial infarction", Science Translational Medicine, 2013, 20 pages, vol. 5, No. 173.
Tous et al., "Injectable Acellular Hydrogels for Cardiac Repair", Journal of Cardiovascular Translational Research, 2011, pp. 528-542, vol. 4.
Yang et al., "A Thermoresponsive Biodegradable Polymer with Intrinsic Antioxidant Properties", Biomacromolecules, 2014, pp. 3942-3952, vol. 15, No. 11.
Yoshitomi et al., "Reactive Oxygen Species-Scavenging Nanomedicines for the Treatment of Oxidative Stress Injuries", Advanced Healthcare Materials, 2014, pp. 1149-1161, vol. 3.
Zhu et al., "Design of a Coupled Thermoresponsive Hydrogel and Robotic System for Postinfarct Biomaterial Injection Therapy", Annals of Thoracic Surgery, 2016, pp. 780-786, vol. 102.

\* cited by examiner

BIODEGRADABLE, ANTIOXIDANT, THERMALLY RESPONSIVE INJECTABLE HYDROGEL AND USES THEREFOR

CROSS REFERENCE TO RELATED APPLICATIONS

This application is the United States national phase of International Application No. PCT/US2017/055564 filed Oct. 6, 2017, and claims the benefit of United States Provisional Patent Application No. 62/405,441 filed Oct. 7, 2016, each of which is incorporated herein by reference.

STATEMENT REGARDING FEDERAL FUNDING

This invention was made with government support under Grant No. HL105911 awarded by the National Institutes of Health. The government has certain rights in the invention.

The production of excessive reactive oxygen species (ROS) causes oxidative stress injuries and is implicated in pathological processes including apoptosis, inflammation and fibrosis associated with myocardial infarction, ischemia and ischemia reperfusion injury, e.g., with myocardial infarction, bowel disease, stroke, and transplantation, diabetes, arthritis and Parkinson's disease. In treating some of these conditions, thermally responsive injectable hydrogels have been used to provide mechanical support and as vehicles for drug and cell delivery. However, compositions that effectively control ROS levels during reperfusion and healing are lacking.

SUMMARY

Provided herein are compositions and methods for reducing ROS accumulation e.g., during healing or reperfusion processes are provided. A biocompatible antioxidant copolymer composition that forms a gel upon injection into a patient and that can maintain ROS scavenging capacity for from days to weeks is provided. Methods of making and using the composition also are provided.

In one aspect, a thermal responsive copolymer composition is provided. The composition comprises a saturated hydrocarbyl backbone, and a plurality of pendant pyrrolidone, antioxidant radical, polyester oligomer, and N-alkyl amide groups, the copolymer having a transition temperature between 10° C. and 35° C., or between 15° C. and 30° C., above which temperature, the polymer composition transitions from an aqueous-miscible state to a higher viscosity partially-miscible or immiscible state in an aqueous solution.

According to further aspects, a method of making an antioxidant polymer composition is provided. The method comprises: polymerizing, using a radical polymerization method, a monomer mixture comprising vinyl pyrrolidone, an acrylate comprising a reactive group, a polyester oligomer acrylate macromer, and an N-alkyl acrylamide; and linking an antioxidant radical moiety to the reactive group.

In further aspects, a method of treating ischemia or an ischemia reperfusion injury in a patient, such as in a cardiac infarct, a chronic wound, a diabetic foot ulcer, CNS tissue, or transplanted tissue. The method comprises administering to a patient at a site of ischemia an antioxidant, thermal-responsive copolymer composition as described herein.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". As used herein, embodiments "comprising" one or more stated elements or steps also include, but are not limited to embodiments "consisting essentially of" and "consisting of" these stated elements or steps.

A "patient" is a human or non-human animal and does not imply or require a doctor-patient or veterinarian-patient relationship.

The term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas co-polymers contain more than one type of monomer. An "oligomer" is a polymer that comprises a small number of monomers, such as, for example, from 3 to 100 monomer residues. As such, the term "polymer" includes oligomers. The terms "nucleic acid" and "nucleic acid analog" includes nucleic acid and nucleic acid polymers and oligomers.

Figure 1A:
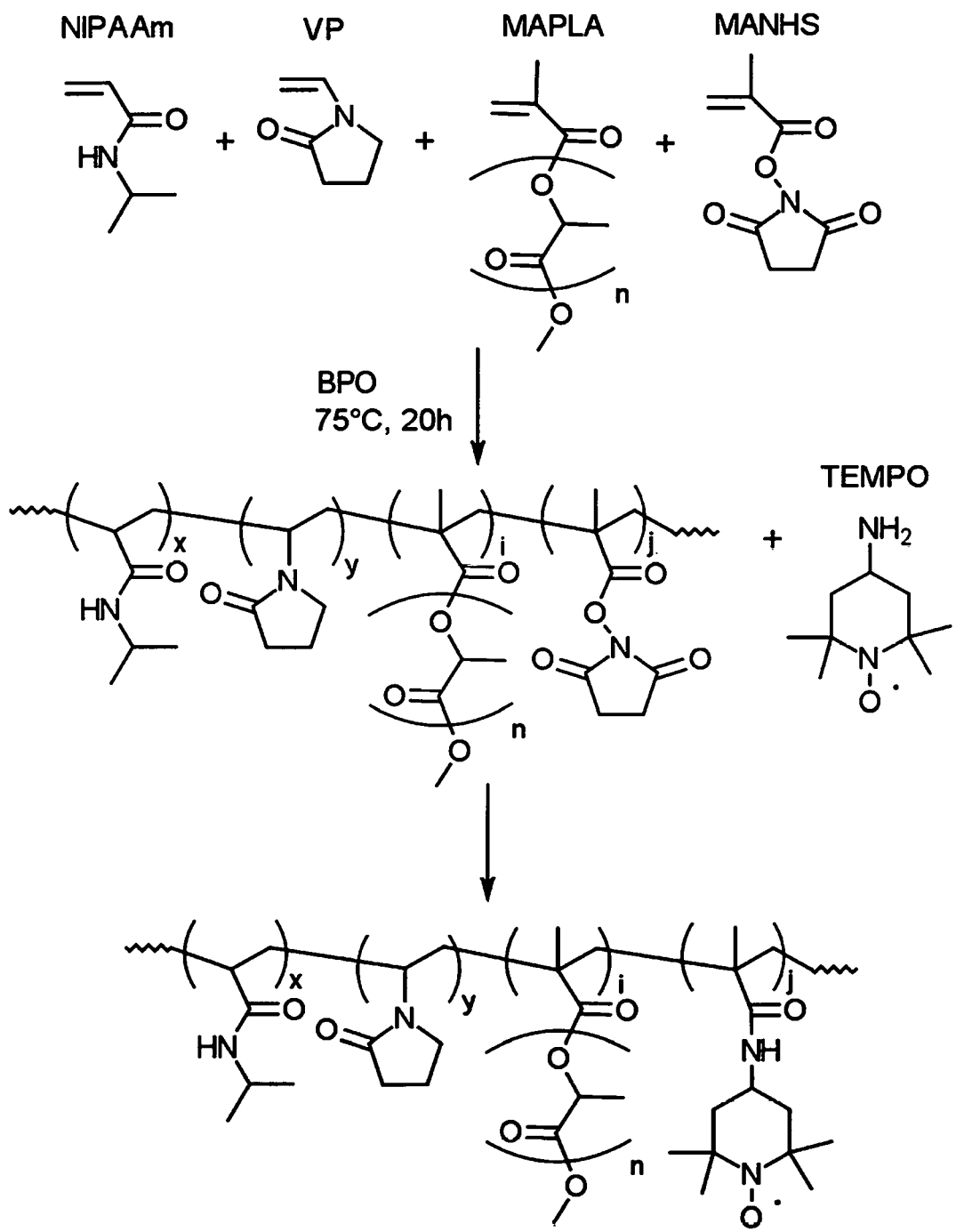
FIG. 1A. Synthesis scheme for Poly(NIPAAm-co-VP-co-MAPLA-co-MANHS) (pNVMM).
Figure 1B:
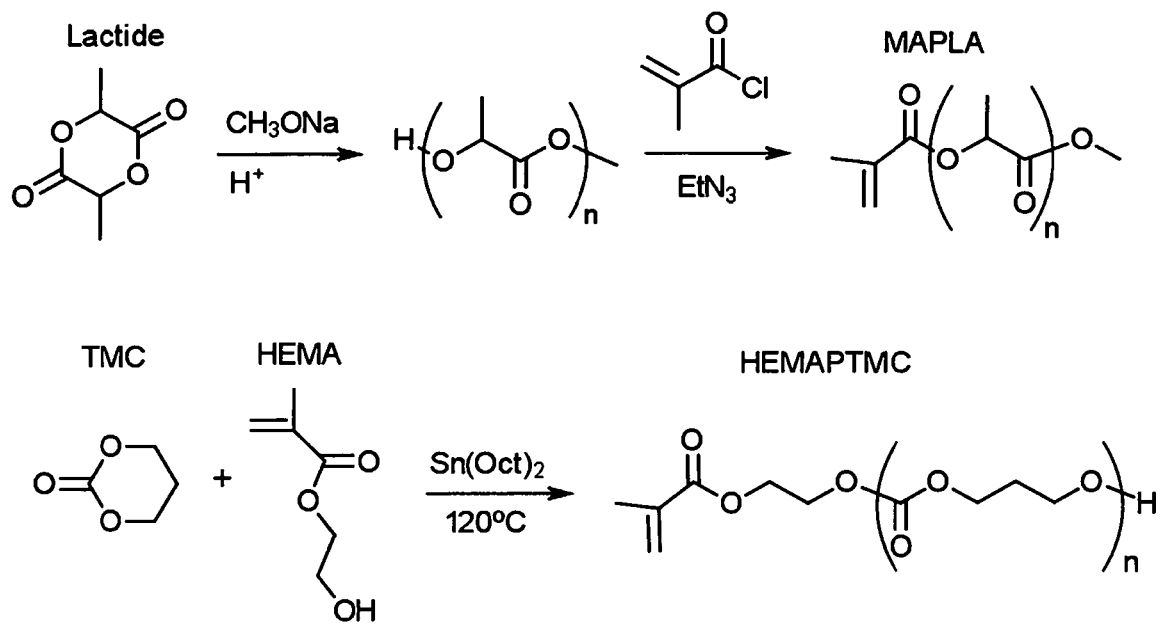
FIG. 1B shows the synthesis scheme for MAPLA (top) and HEMAPTMC (bottom), 0>n<10.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain linking groups are incorporated into the polymer backbone or certain groups are removed in the polymerization process. A polymer is said to comprise a specific type of linkage if that linkage is present in the polymer. An incorporated monomer is a "residue". Non-limiting examples of monomers, in the context of the copolymers described herein, include: acrylate or acrylamide monomers, acrylate N-hydroxysuccinimide ester monomers, N-hydroxysuccinimide methacrylate monomers, acrylate or methacrylate forms of N-acryloxy succinimide (NAS) monomers, hydroxyethyl methacrylate monomers, methacrylate monomers, acrylate or methacrylate forms of lactide monomers, and acrylate or methacrylate forms of trimethylene carbonate (TMC) monomers. As described in further detail below, a monomer may be a macromer prepared from smaller monomers, such as a hydroxyethyl methacrylate-polylactide (HEMAPLA) macromer, a hydroxyethyl methacrylate-poly(trimethylene carbonate) (HEMAPTMC) macromer, or a methacrylate-polylactide (MAPLA) macromer (see, e.g., FIG. 1B, described below).

A "moiety" (pl. "moieties")) is a part of a chemical compound, and includes groups, such as functional groups. As such, as therapeutic agent moiety is a therapeutic agent or compound that is modified by attachment to another compound moiety, such as a polymer monomer, e.g., the nucleic acid or nucleic acid analog monomers described herein, or a polymer, such as a nucleic acid or nucleic acid analog as described herein.

"Alkyl" refers to straight, branched chain, or cyclic hydrocarbon (hydrocarbyl) groups including from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" refer to divalent alkyl and divalent substituted alkyl, respectively, including, without limitation, ethylene (—CH$_2$—CH$_2$—). "Optionally substituted alkylene" refers to alkylene or substituted alkylene.

The term "acrylate" refers to a 2-propenoate group, and includes acrylic acid or $CH_2C(R_1)C(O)OR$ (a 2-propenoate). "Acrylamide" is a prop-2-enamide, e.g., having the structure $CH_2C(R_1)C(O)N(R)_2$. In each instance R1 is H or lower alkyl, such as methyl ("methacrylate"), and where R is any compatible moiety of group, such as, without limitation, a hydrocarbyl group, an alkyl group (e.g. NIPAAm is an acrylamide where R is n-propyl), an antioxidant, or a reactive group.

In the synthesis of any composition described herein, any reactive group may be protected using a protecting group, as are broadly-known in the art. "Protecting groups" include, without limitation: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), dimethoxytrityl (DMT), 1-(4,4-dimethyl-2,6-dioxacyclohexylidene)ethyl (Dde), diathiasuccinoyl (Dts), benzothiazole-2-sulfonyl (Bts) and monomethoxytrityl (MMT) groups.

"Cycloalkyl" refer to monocyclic, bicyclic, tricyclic, or polycyclic, 3- to 14-membered alkyl ring systems, which are either saturated, unsaturated or aromatic. The cycloalkyl group may be attached via any atom. Cycloalkyl also contemplates fused rings wherein the cycloalkyl is fused to an aryl or hetroaryl ring, including spiro fused. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below.

"Hetero atom" refers to N, O, P, and S. "Hetero-substituted" refers to an organic compound in any embodiment described herein in which one or more carbon atoms are substituted with N, O, P or S. Alkyl and hydrocarbyl groups according to any aspect described herein, can comprise one or more hetero atoms.

Reactive oxygen species (ROS) include hydrogen peroxide ($H_2O_2$), hydroxyl radical (HO$^•$), nitric oxide (NO), peroxy radical (ROO$^•$), peroxynitrite anion ONOO$^-$), singlet oxygen ($^1O_2$), and the superoxide radical anion ($^•O_2^-$). ROS have physiological roles, but in certain circumstances, such as in ischemia and reperfusion, ROS levels can reach harmful levels, or levels that can prevent proper tissue growth and recovery. As used herein, an "antioxidant" is an ROS scavenger, and is thereby able to reduce oxidative stress, and antioxidant moieties are (antioxidant) ROS scavengers that are covalently linked to other chemical moieties, such as an acrylate, or a copolymer as described herein. Non-limiting examples of useful antioxidant compounds useful for attachment to the copolymers described herein, and therefore for use as antioxidant moieties as described herein include: 4-Hydroxy-TEMPO (TEMPOL, 4-hydroxy-2,2,6,6-tetramethylpiperidine 1-oxyl), 4-carboxy-TEMPO (4-carboxy-2,2,6,6-tetramethylpiperidine 1-oxyl), 4-Cyano-TEMPO (4-cyano-2,2,6,6-tetramethylpiperidine 1-oxyl), 4-amino-TEMPO (4-amino-2,2,6,6-tetramethylpiperidine 1-oxyl), 3β-DOXYL-5α-cholestane (4',4'-dimethylspiro (5α-cholestane-3,2'-oxazolidin)-3'-yloxy), 5-DOXYL-stearic acid (2-(3-carboxypropyl)-4,4-dimethyl-2-tridecyl-3-oxazolidinyloxy), 16-DOXYL-stearic acid (2-(14-carboxytetradecyl)-2-ethyl-4,4-dimethyl-3-oxazolidinyloxy), methyl 5-DOXYL-stearate (2-(4-methoxy-4-oxobutyl)-4,4-dimethyl-2-tridecyl-3-oxazolidinyloxy), 3-(aminomethyl)-PROXYL (3-(aminomethyl)-2,2,5,5-tetramethyl-1-pyrrolidinyloxy), α,γ-bisdiphenylene-β-phenylally, 3-carbamoyl-PROXYL (3-carbamoyl-2,2,5,5-tetramethylpyrrolidin-1-yloxy), 3-carbamoyl-2,2,5,5-tetramethyl-3-pyrrolin-1-oxyl, 3-carboxy-PROXYL (3-(carboxy)-2,2,5,5-tetramethyl-1-pyrrolidinyloxy), 3-cyano-PROXYL (3-cyano-2,2,5,5-tetramethyl-1-pyrrolidinyloxy), Galvinoxyl (2,6-di-tert-butyl-α-(3,5-di-tert-butyl-4-oxo-2,5-cyclohexadien-1-ylidene)-p-tolyloxy), 4-(1-hydroxy-1-methylethyl)-2,2,5,5-tetramethyl-3-imidazolinium-1-yloxy, 3-(2-iodoacetamido)-PROXYL (3-(2-Iodoacetamido)-2,2,5,5-tetramethyl-1-pyrrolidinyloxy), 3-maleimido-PROXYL (3-maleimido-2,2,5,5-tetramethyl-1-pyrrolidinyloxy), 4-phenacylidene-2,2,5,5-tetramethyl-imidazolidin-1-yloxy, 4-phenyl-2,2,5,5-tetramethyl-3-imidazolin-1-yloxy, 2,2,5-trimethyl-4-phenyl-3-azahexane-3-nitroxide, and tris(4-bromophenyl)ammoniumyl, all of which are commercially available as stand-alone compounds, and which can be linked to the copolymer compositions described herein by known linking reactive groups and known methodologies. Antioxidants comprising a nitroxide radical are referred to as "nitroxide antioxidants", such as TEMPO.

The polymer compositions described herein are thermal-responsive, and transition from a solution (miscible in an aqueous solution or solvent) to a hydrogel (immiscible in an aqueous solution or solvent, thereby excluding at least a portion of the solvent) as the temperature of the composition is raised, for example, they are a solution at a temperature above freezing (e.g., 0° C.) and below physiological temperatures (normal body temperature of a patient, e.g., between 35° C. and 42° C.) and form a hydrogel state or phase at physiological temperatures. The temperature of transition from solution to gel in a given system is referred to herein as the lower critical solution temperature (LCST) of the hydrogel. Thus, the compositions described herein, the composition are a solution at a temperature below a specified temperature (e.g., at a temperature below 35° C.) and a hydrogel at a temperature ranging from 35° C. to 42° C., inclusive.

At a temperature less than the transition temperature, e.g. LCST, the hydrogel flows easily and can be injected into a patient. When the temperature is increased above the transition temperature, e.g., the LCST, the viscosity of the composition increases, and if the composition does not diffuse into tissue, it forms a hydrogel mass or plug. The hydrogel is highly flexible and relatively strong at physiological temperature. For complete removal of the copolymer over time (for example and without limitation, from one to 12 weeks), the copolymer includes hydrolytically-cleavable polyester bonds that, upon degradation in situ, results in soluble, non-toxic by-products, and which also results in dissolution of the degraded hydrogel and clearance of the degraded components. In another aspect, when ester linkages in the composition are hydrolyzed (for instance over time in situ in a living system, such as a human patient), the released copolymer fragments have an LCST above 37° C., so that they are soluble (and as an additional benefit, non-toxic), facilitating safe degradation and clearance of the polymer over time in a living system such as a human body.

The LCST of a polymer composition can be determined by measuring the change in transmittance with a UV-Vis spectrometer as a function of temperature. LCST also can be determined by any other useful method—for example and without limitation by Differential Scanning Calorimetry (DSC).

In one aspect, the copolymer has a lower critical solution temperature or transition temperature below 37° C., for example 36° C. or lower, 35° C. or lower, 34° C. or lower, or, in another aspect between 10° C. and 34° C., including increments and sub-ranges therebetween, and in another aspect, less than 20° C. The polymer composition can be distributed through the marketplace, stored and administered to a patient as a liquid at ambient temperatures (or, if necessary, maintained at a cool temperature with an ice-pack, refrigerator or other cooling device), and the polymer gels as it warms past its LCST. Many polymers suitable for administration to patients require mixing of monomers immediately prior to use, which is undesirable for many reasons. For instance, it is impractical to ask doctors, nurses or technicians to mix monomers at the time they need the polymer. Further, monomers can have varying degrees of toxicity. The copolymers described herein do not require conducting a chemical reaction at the site of use and the copolymers can be washed free of monomer contamination prior to distribution in the marketplace. Lastly, the release of a portion of the aqueous phase during phase transition can facilitate local drug delivery in the excluded aqueous phase.

The copolymers, compositions and components thereof are biocompatible when used for medical or veterinary purposes. By "biocompatible," it is meant that a polymer composition and its normal in vivo degradation products are cytocompatible and are substantially non-toxic and non-carcinogenic in a patient within useful, practical and/or acceptable tolerances. By "cytocompatible," it is meant that the copolymers or compositions are substantially non-toxic to cells and typically and most desirably can sustain a population of cells and/or the polymer compositions, devices, copolymers, and degradation products thereof are not cytotoxic and/or carcinogenic within useful, practical and/or acceptable tolerances. For example, a copolymer composition when placed in a human epithelial cell culture does not adversely affect the viability, growth, adhesion, and number of cells. In one non-limiting example, the co-polymers, compositions, and/or devices are "biocompatible" to the extent they are acceptable for use in a human or veterinary patient according to applicable regulatory standards in a given legal jurisdiction. In another example the biocompatible polymer, when implanted in a patient, does not cause a substantial adverse reaction or substantial harm to cells and tissues in the body, for instance, the polymer composition or device does not cause significant necrosis or an infection resulting in harm to tissues organs or the organism from the implanted compositions.

According to aspects of the compositions described herein, provided herein are injectable compositions that are biodegradable, elastomeric and thermoresponsive and which can easily take the shape of a cavity into which they are injected, or diffuse into tissue at the site of injection in advance of phase transition to a solid hydrogel. The copolymers are injectable as a liquid at or below body temperature (about 37° C.) or room temperature (about 25° C.), or at a temperature in the range of from 4° C. to 30° C., and form gels at body temperature. These materials are useful for a number of purposes. For example, in treatment of reperfusion injury, e.g., in myocardial infarcts, or transplants, as an injectable stem cell niche for bone marrow transplants, or for other transplantation settings; as delivery vehicles for chemotherapy to tissue, such as, for example and without limitation, gut following tumor resections; sealants for pulmonary and neural applications as well as for emergency treatment of wounds. The materials also can find use as bulking agents for cosmetic applications or, even more generally, rheology modifiers. In one embodiment, the compositions are injected in a heart for repair or regeneration of cardiac tissue.

In aspects, the composition is injected into the heart, to treat a heart defect or to treat and infarct or reperfusion injury. In some embodiments, the composition is injected into myocardial tissue, at the site of a myocardial defect. In some embodiments, the myocardial defect is necrotic tissue. In some embodiments, the necrotic myocardial tissue is an infarct that is the result of a myocardial infarction. Those of skill in the art will understand and appreciate that the composition described above is suitable for such therapeutic uses because of its characteristics, specifically its flowable, liquid nature at room temperature (or below the temperature of the human body), and gel-like nature at physiological temperatures (such as 37° C.). Thus, a practitioner may deliver the proper amount of the composition with precision, and without the worry of the composition "running" into areas where it is not wanted or needed. In aspects, the composition, e.g. a tissue-diffusable embodiment thereof, is injected into, coated onto, or otherwise contacted with a transplanted tissue (graft), such that the composition diffuses into the tissue prior to implantation of the tissue in a patient.

In aspects, the copolymers and compositions comprising the copolymers may serve, for example, as adhesives or fillers. They may be applied to wounds or into body cavities or used as a tissue packing to apply compression. As such, embodiments of the copolymer solutions described herein may be applied to wounds and, in one embodiment covered, optionally with a warming compress or "heat pack" for example as are available commercially to ensure that the copolymer is maintained at a temperature above its LCST and thus remains gelled when in contact with any cooler areas of the body, typically the skin. As a hydrogel, embodiments of the copolymers disclosed herein may be contained in a composition comprising the copolymer and an aqueous solution that does not interfere substantially with the LCST and polymer structure in its intended use.

According to one aspect, in its application to wound treatment, a clotting agent such as desmopressin may be included in a polymer composition. An appropriate, e.g., pharmaceutically acceptable, foaming agent as are well-known in the relevant arts also may be included for the purpose of creating compression in a wound, whether exposed to a body surface in the case of (for example) puncture wounds or bullet wounds, or internal wounds, in which case, the polymer can be injected into or near a site of internal bleeding. As such, the composition can find use in many situations, ranging from home use to stabilization of bleeding or massively bleeding patients in emergency and battlefield situations. The copolymer also can be used during surgical procedures to apply compression and otherwise secure a site of injury, such as a portion of a patient's intestine, nasal passage or sinus cavity where a tumor or polyp has been removed or after other surgeries.

In one aspect, the copolymer composition is a copolymer of N-vinyl pyrrolidone, an acrylate monomer, a polyester acrylate macromer, and an acrylic monomer modified with an antioxidant moiety. The acrylate monomer is a form of vinyl monomer, and includes acrylic and methacrylic monomers, including acrylamides, examples of which include: alkyl acrylates, such as alkyl acrylamides, or $C_{1-4}$ alkyl acrylamides. Acrylates therefore include as a class, for example and without limitation: n-isopropylacrylamide (NIPAAm), hydroxyethyl methacrylate (HEMA), methacrylic acid (MAA); and acrylic acid (AA). The copolymer composition comprises residues of the monomers used to manufacture the composition. Because the copolymer is a polyvinyl polymer, it has a hydrocarbyl backbone with pendant groups including the antioxidant moiety, such as TEMPO, and polyester moiety from the polyester acrylate macromer, such as polylactide from MAPLA or polyTMC from HEMA-PTMC, as well as other remaining groups of the monomers used to manufacture the copolymer. The compositions described herein include an aqueous (water-based) solvent, for example and without limitation, water, saline, and phosphate-buffered saline, and are therefore described as hydrogels.

The polymer comprises a polyester acrylate macromer comprising an acrylate moiety and a polyester moiety. Polyester macromers are compounds containing on the average more than one, e.g., two or more ester linkages. In the context of macromer and polymer preparations, unless otherwise indicated, the number of residues indicated as being present in a given polymer or macromer is an average number and is not to be construed as an absolute number. Thus, as a non-limiting example, in the context of the described macromers, the number of monomers in the polyester moiety of the macromer may be an integer or any number, such as 2.1, 3.9 and 7.0, referring refer to an estimated average number of monomer residues present in the polyester moiety of the macromer composition. The average number of residues may be determined by any method, for example and without limitation, by $^1$H-NMR. In aspects, the polyester moiety has, for example and without limitation, an average of ten or less ester linkages. Non-limiting examples of the polyester acrylate macromer include a macromer comprising methacrylate moiety and a polylactide moiety (MAPLA), or a hydroxyethyl methacrylate moiety and a polytrimethylcarbonate moiety (HE-MAPTMC). In one aspect, the macromer is a MAPLA, and the ratio of methacrylate and lactide residues in the polyester macromer ranges from 1:2 (methacrylate:lactide) to 1:8, in another, from 1:1 to 1:10, such as 1:1, 1:2, 1:3, 1:4, 1:5, 1:6, 1:7, 1:8, 1:9, and 1:10. In another aspect, for a HEMA-PTMC macromer, the ratio of hydroxyethyl methacrylate and trimethylene carbonate residues in the polyester macromer ranges from 1:1 to 1:10, 1:2 to 1:5 or any increment within those ranges, including 1:1, 1:2, 1:3, 1:4, 1:4.2, 1:5, 1:6, 1:7, 1:8, 1:9, and 1:10.

Due to the possibility of an antioxidant group interfering with radical polymerization, the acrylic monomer modified with an antioxidant moiety can be prepared by modifying a polyvinyl (polyacrylic) polymer with an antioxidant. In aspects, the polymer is prepared with a vinyl or acrylic monomer comprising a reactive group, such as, without limitation, N-hydroxysuccinimide, hydroxyl, carboxyl, amine, sulfhydryl, cyano, or oxirane, resulting in a pendant reactive group that can later be reacted with an antioxidant compound, such as the reaction of N-hydroxysuccinimide with 4-amino TEMPO as described herein.

In one aspect, an amine-reactive reactive group is included in the copolymer. Non-limiting examples of amine-reactive group includes: a succinimide group, an oxysuccinimide group, and an isocyanate group, such as is produced by incorporation of N-hydroxysuccinimide methacrylate (MANHS) or N-acryloxy succinimide (NAS) monomers into the copolymer. The amine-reactive groups bind to amine-containing compounds including amino group-containing antioxidants, such as 4-amino TEMPO. Varying amounts of the amine-reactive component may be used, depending on the desired density of amine-reactive groups, while maintaining desirable physical and degradation properties of the resultant copolymer.

In one aspect, along with the antioxidant acrylate residue, the copolymer composition comprises N-isopropylacrylamide (NIPAAm) residues, hydroxyethyl methacrylate (HEMA) residues, polyester macromer methacrylate-polylactide (MAPLA) macromer residues, and methacrylic acid (MAA) monomers. Alternately, the copolymer comprises NIPAAm residues, acrylic acid (AAc) residues, the polyester macromer hydroxyethyl methacrylate-poly(trimethylene carbonate) (HEMAPTMC) macromer residues, and MAA monomers.

Alternatives for NIPAAm residues include N-alkyl acrylamide residues in which the alkyl is one of methyl, ethyl, propyl, isopropyl and cyclopropyl. Alternatives for HEMA include (hydroxyl $(C_1-C_3)$alkyl)methacrylate and other methacrylate substituents that can modulate the LCST of the polymer. Although the size of the copolymers can vary, in one example, the copolymer has a $M_n$ of between 20 kD and 35 kD. In another example, the copolymer has a polydispersity index (PDI, $M_w/M_n$) of between 1 and 2.

According to another aspect, along with the antioxidant acrylate residue, the copolymer composition comprises NIPAAm residues, N-vinylpyrrolidone monomers (VP), and MAPLA macromer residues, or NIPAAm residues, N-vinylpyrrolidone monomers (VP), and hydroxyethyl methacrylate-poly(trimethylene carbonate) (HEMA-PTMC) macromer residues.

Alternately, the copolymer comprises NIPAAm residues, VP monomers, and the polyester macromer hydroxyethyl methacrylate-poly(trimethylene carbonate) (HEMA-PTMC) macromer residues. Alternatives for NIPAAm residues in this embodiment include N-alkyl acrylamide residues in which the alkyl is one of methyl, ethyl, propyl, isopropyl and cyclopropyl. Alternatives for HEMA include (hydroxyl ($C_1$-$C_3$)alkyl)methacrylate and other methacrylate substituents that can modulate the LCST of the polymer. Although the size of the copolymers can vary, in one example, the copolymer has a $M_n$ of between 20 kD and 35 kD. In another example, the copolymer has a polydispersity index (PDI, $M_w/M_n$) of between 1 and 2.

In describing ratios of respective monomers for any given copolymer, it is convenient to refer to feed ratios of the monomers in respect to the polymerization method used to produce the copolymer, for example and as used herein, in reference to the radical polymerization methods used to prepare the copolymers. This is especially so when considering that the products of the polymerization process are polydisperse and are often random in their composition. The feed ratios typically closely represent the ratios of monomer residues in the copolymer, but typically do not exactly match because certain monomers incorporate more efficiently than others in any given copolymer composition. The actual ratios of monomer residues typically vary less than 10%, and often less than 5% of the feed ratios. As used herein a "feed ratio" refers to a feed ratio in a typical radical polymerization method, such as the methods described in the examples below and the ranges described herein.

The ability of the described copolymer compositions to diffuse into tissue or to form a discrete hydrogel body or plug can be tailored by changing the hydrophilicity of the composition. For example, increased vinylpyrrolidone content (increased % wt. % of residues, or % of monomers used in the polymerization of the polymer (feed ratio)) results in a more hydrophilic copolymer composition that can diffuse into tissue as opposed to forming a discrete hydrogel body. While the increased VP content changes the ability of the composition to diffuse in tissue, it also can affect the transition temperature for temperature-dependent gelation. However, where the transition temperature remains below 37° C., when injected and diffused within the tissue, the polymer transitions to a state of increased viscosity.

Additional variations on the above-described copolymer compositions having pendant antioxidant and polyester moieties and having a desired solution to gel thermal transition temperature, and tissue diffusion, can be prepared by a person of ordinary skill using the various monomers described herein.

The composition also can include an active agent, such as, without limitation, one or more of an antiseptic, an antibiotic, an analgesic, an anesthetic, a chemotherapeutic agent, a clotting agent, an anti-inflammatory agent, a metabolite, a cytokine, a chemoattractant, a hormone, a steroid, a protein and a nucleic acid. In one aspect, the composition comprises a clotting agent, one example of a clotting agent is desmopressin. In another aspect, for use (e.g.) in repair of cardiac tissue, the active agents are one or both of bFGF and IGF-1. A biological material, such as a cell or a virus particle may also be incorporated into the composition.

Monomers (including as a group macromers) can be introduced into the copolymer by radical polymerization or other polymerization methods, such as living polymerization (e.g., atom transfer radical polymerization), or in any useful manner using any suitable initiator, such as benzoyl peroxide. These polymerization processes are well-known in the polymer chemistry field. Radical polymerization is one of the most widely used methods for preparing high polymer from a wide range of vinyl monomers. Although radical polymerization of vinyl monomers is very effective, it does not allow for the direct control of molecular weight, control of chain end functionalities or for the control of the chain architecture, e.g., linear vs. branched or graft polymers. Living polymerization systems have been developed which allow for the control of molecular weight, end group functionality, and architecture. ATRP is a type of controlled radical polymerization or living radical polymerization. (see, e.g., U.S. Pat. Nos. 5,763,548, 5,807,937, 5,789,487, 6,541,580, and 7,678,869). Controlled radical polymerization methods facilitate production of precise polymer, copolymer and block copolymer structures, such as A-B-A structures.

In aspects, a method is therefore provided of making a thermosensitive antioxidant copolymer, for example and without limitation, a co-polymer described herein, the method comprising co-polymerizing vinyl pyrrolidone, an acrylate or acrylamide monomer, a polyester acrylate macromer, and an acrylate and/or acrylamide monomer having a reactive group, for example, copolymerizing NIPAAm, VP, MANHS, and a polyester macromer, and attaching an antioxidant moiety, such as TEMPO, to the copolymer. Although feed ratios can be varied to optimize structure and function, exemplary feed ratios are provided in Table 1.

TABLE 1

| Monomer | Mole % in feed |
| --- | --- |
| vinyl pyrrolidone | 4%-20%, e.g., 10%-20% |
| acrylate or acrylamide monomer | 70%-90%, e.g., 75%-85% |
| polyester acrylate macromer | 4%-10% |
| acrylate and/or acrylamide monomer having a reactive group, e.g., MANHS | 0.01%-10% |

In aspects, copolymers comprise, are prepared from, or consist essentially of combinations of four types of subunits/residues: 1) N-alkyl acrylamide in which the alkyl is methyl, ethyl, propyl, isopropyl or cyclopropyl, for example N-isopropylacrylamide; 2) N-vinylpyrrolidone (VP); 3) a methacrylate-polylactide (MAPLA) macromer; and 4) an acrylate or acrylamide comprising a reactive group (RGA), such as MANHS. In non-limiting examples, the MAPLA macromer has a lactide:methacrylate ratio of at least 1:1, or in the range of 2-4:1 (that is, ranging from 2:1 to 4:1). In some aspects, the feed ratio (in mole percent) for NIPAAm:VP:MAPLA is 75-85:5-20:5-10, wherein (NIPAAm+MAPLA):(VP+RGA)=85-95:5-15 (inclusive of values between those provided here). In one aspect, the feed ratio of RGA ranges from 0.01 to 10. In one aspect, the feed ratio of NIPAAm:VP:MAPLA is in the range of 70-90:4-20:4-20. In one example, the feed ratio of VP is 10, such that the feed ratio of NIPAAm:VP:MAPLA is 75-85:10:5-10, for example and without limitation, in one embodiment, the feed ratio of NIPAAm:VP:MAPLA is be one of 80:10:10 or 85:10:5. In another embodiment, the feed ratio of VP is 15, such that the feed ratio of NIPAAm:VP+RGA:MAPLA is 75-85:15:5-10. In one embodiment the feed ratio is 80:15:5.

The degradation rate is positively correlated to the amount of VP included in the composition, that is, less VP leads to decreased degradation. Degradation of a copolymer hydrogel formed as described herein is typically 200 days and less, depending on VP content. Those of skill will easily be able to fine-tune the VP content to match a preferred degradation rate. As described above, by degradation it is meant that the copolymer (and/or hydrogel formed from said copolymer) is substantially degraded at the indicated time point, with percentage degraded (or percentage remaining) being as described above. In some embodiments, the hydrogel degrades in less than 100 days, less than 90 days, less than 80 days, less than 70 days, less than 60 days, less than 50 days, less than 40 days, less than 30 days, less than 20 days, less than 10 days, or less than 5 days.

Reference is made to International Patent Publications: WO 2008/045904 and WO 2010/127254, for the disclosure of the general process of making, and characteristics of, various copolymers that can be modified to include pendant antioxidant moieties as described herein, the disclosures of which are incorporated herein by reference in their entirety.

In aspects, a method of treating ischemia, such as a reperfusion injury, for example in a myocardial infarct or transplanted tissue, is provided. The method comprises injecting or otherwise introducing a composition comprising an antioxidant copolymer according to any aspect herein, for example, N-alkyl acrylamide residues in which the alkyl is one of methyl, ethyl, propyl, isopropyl and cyclopropyl; vinylpyrrolidone residues; polyester acrylate macromer residues; and antioxidant acrylate residues into (within, in contact with, or in tissue surrounding) ischemic tissue, such as an infarct. The injection of either of the above general class of copolymers may take place from 1 day to 21 days after infarction (inclusive of values between those provided here). In an embodiment, the injection of the composition occurs between 7 and 14 days (inclusive of values between those provided here) following infarction, so as to maximize functional outcome through tissue remodeling while allowing time for the patient to recover from the insult.

According to another aspect, a method of growing cells is provided, comprising introducing cells into any copolymer composition described herein by contact or mixing with cells, to produce a cell construct and incubating the cell construct under conditions suitable for growth of the cells, including in vivo. The composition can comprise cell growth media to facilitate cell growth within the composition. The cell construct can be administered to a patient (placed in a patient's body at a desired location), such as a human patient. In one aspect, the composition is administered to a patient without cells, but so that the patient's cells migrate into the composition. The composition can be administered by an injection into the desired site, such as cardiac tissue within the patient.

For example, the composition may be injected in or around ischemic or necrotic tissue in the heart. In one aspect, the composition is injected immediately after, to within one month after the patient has an ischemic event, such as a myocardial infarction, or transplantation. This injection may take place multiple times to account for degradation of the copolymer composition and/or loss of antioxidant effect, though TEMPO and other antioxidants can regenerate. The composition also may include one or more active agents, such as, without limitation, an antiseptic, an analgesic, an anesthetic and an antibiotic. To facilitate heart repair, or repair of any tissue, or cell growth in general, the composition may comprise, with or without other active agents, one or more of a cytokine, a cell growth or differentiation agent and a metabolite, such as one or both of bFGF and IGF-1.

Compositions comprising a copolymer described herein can be distributed for use in any suitable vessel. In one aspect, the composition is packaged in a sealed container, from which the composition can be poured, squeezed or otherwise decanted, for example and without limitation, by use of a syringe. The vessel can be a bag, such as an IV bag. In another aspect, the composition can be distributed in a syringe for immediate dispensation into a wound or body cavity/location. A syringe can be fitted with any type of needle, tip, tube, balloon device or other useful fitting for facilitating accurate placement of the solution in or around a desired delivery site, for example and without limitation, for delivery into the large intestine of a patient after removal of a tumor. In another aspect, the composition and a pharmaceutically acceptable solvent is stored within a syringe at or below 4° C. and the syringe is fitted with a needle gauge sufficient to allow for injection without increased pressure but also prohibit back flow of the solution into the syringe after injection, such as, without limitation, a 16 G through 23 G (gauge) needle, and in certain embodiments an 18 G or 20 G needle. As described below and in the Examples, a robotic injection device can be used to deliver any of the compositions described herein to the heart or other organs or tissue. Thus, methods of use embodying the above-described uses for a copolymer described herein and compositions comprising the copolymer are contemplated and embraced as part of the present invention.

In the context of myocardial infarction, although myocardial injection therapy is currently dominated by transcatheter endocardial approaches, direct epicardial injection offers potential advantages such as easy detection of target myocardial infarct lesions, decreased likelihood of cerebrovascular complications, and superior site specific efficacy. Particularly with gel materials, the risk of backflow and embolization from an endocardial injection site is a serious concern. To date, a major limitation of direct epicardial injection is the lack of dedicated minimally invasive access technology, generally causing it to be performed only in conjunction with other procedures using sternotomy or thoracotomy, both of which have high associated morbidity. In addition, the instrumentation used in most reported applications does not readily accommodate the motion of the beating heart, and therefore does not facilitate precise placement and depth of injections. A dedicated technology for precise interaction with the heart from within the intrapericardial space that balances treatment efficacy and minimal invasiveness is likely to provide a future clinical benefit for the hydrogel injection therapy proposed here and for myocardial injection-based therapies in general. A device, such as that described in U.S. Patent Application Publication No. 20050154376, which navigates over the epicardial surface to perform minimally invasive myocardial injections on the beating heart through a subxiphoid approach may be used to inject the composition described herein, providing multitarget injection patterns.

The following examples are provided for illustration purposes and are not intended to limit the scope of the present invention.

EXAMPLES

To endow hydrogels with more therapeutic benefit, we report here the development of a biodegradable, injectable hydrogel poly(NIPAAm-co-VP-co-MAPLA-co-MATEMPO) (pNVMT, NIPAAm: N-isopropylacrylamide, VP: vinylpyrrolidone, MAPLA: methacrylate-polylactide, MATEMPO: methacrylate-TEMPO) incorporating an ROS scavenger, 2,2,6,6-tetramethylpiperidine-1-oxyl (TEMPO). In this design, the hydrogel is able to diffuse through the tissue bed upon injection and gel, allowing persistent access to ROS for TEMPO as TEMPO is covalently attached to the polymer chain. The antioxidant activity of the pNVMT hydrogel was evaluated in cell culture under oxidative stress. A rat myocardial infarction/reperfusion model was employed to test the injectability and distribution of the hydrogel in the ROS-laden tissue bed.

Figure 2:
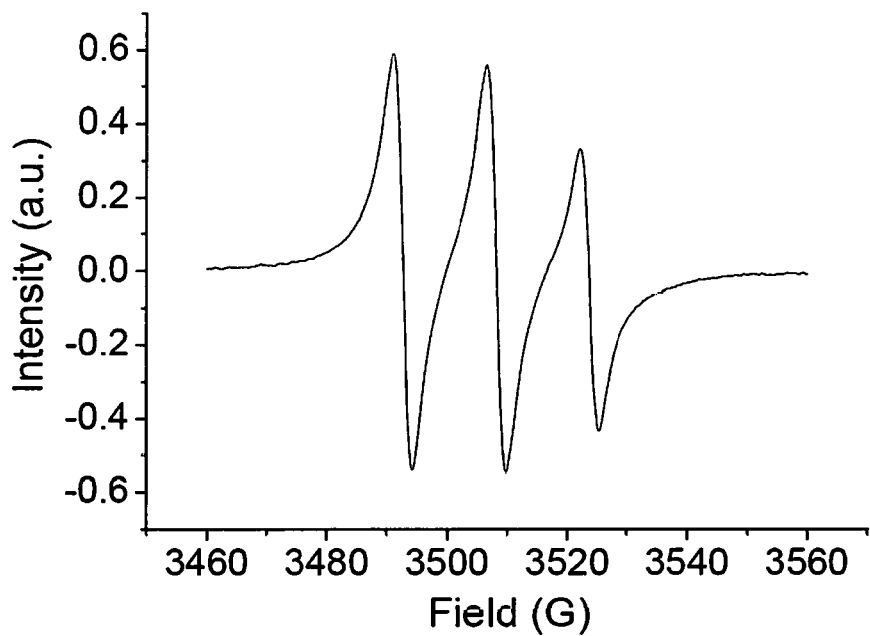
FIG. 2. Electron paramagnetic resonance (EPR) spectrum of pNVMT.

Poly(NIPAAm-co-VP-co-MAPLA-co-MANHS) (pNVMM) was synthesized (FIG. 1A) from Nisopropylacrylamide (NIPAAm), vinylpyrrolidone (VP), methacrylate-polylactide (MAPLA, see FIG. 1B) and methacrylic acid N-hydroxysuccinimide ester (MANHS) by free radical polymerization with a feed ratio of 80:15:5:5. 4-amino-TEMPO or cyclohexylamine was attached to pNVMM at room temperature for 12 hours to obtain poly(NIPAAm-co-VP-co-MAPLA-co-MATEMPO) (pNVMT) and its analog respectively. Attached TEMPO in the copolymer was quantified with electron paramagnetic resonance (EPR) spectroscopy. The degradation and thermal responsiveness were studied for pNVMT and the analog. The antioxidant properties of pNVMT were evaluated with the ROS-producing Fenton reaction and pyrogallol assay. The capacity of pNVMT to protect cells against oxidative stress was evaluated by smooth muscle cells (SMCs) culture: 500 µM $H_2O_2$ was added to the media with or without the pNVMT hydrogel. Intracellular ROS levels, mitochondrial function and cell survival were characterized. pNVMT was injected into infarcted hearts followed by reperfusion in live rats. The distribution of injected pNVMT in the myocardium was determined by magnetic resonance imaging (MRI).

pNVMM was successfully synthesized and TEMPO was covalently bound to the copolymer, generating pNVMT, as confirmed by EPR (FIG. 2). The weight percentage of TEMPO in pNVMT was determined to be 6.1% by EPR. The analog with similar structure but without the nitroxide radicals was also synthesized as the control group. The transition temperature of pNVMT and its analog were 24.1° C. and 21.3° C., respectively. As a result, pNVMT could be injected into tissue at low temperature, diffuse into the tissue bed, and subsequently gel. The diffusability of pNVMT would facilitate better access to the ROS species distributed in the target tissue, which is critical for the TEMPO groups to effectively scavenge. By two weeks both pNVMT and the polymer analog had lost 50% of their mass in PBS at body temperature, as a result of the solubility increase caused by the degradation of MAPLA sidechain. This shows the potential of pNVMT to stay in the target tissue for a relatively long period while covalently carrying the TEMPO group.

Figure 3:
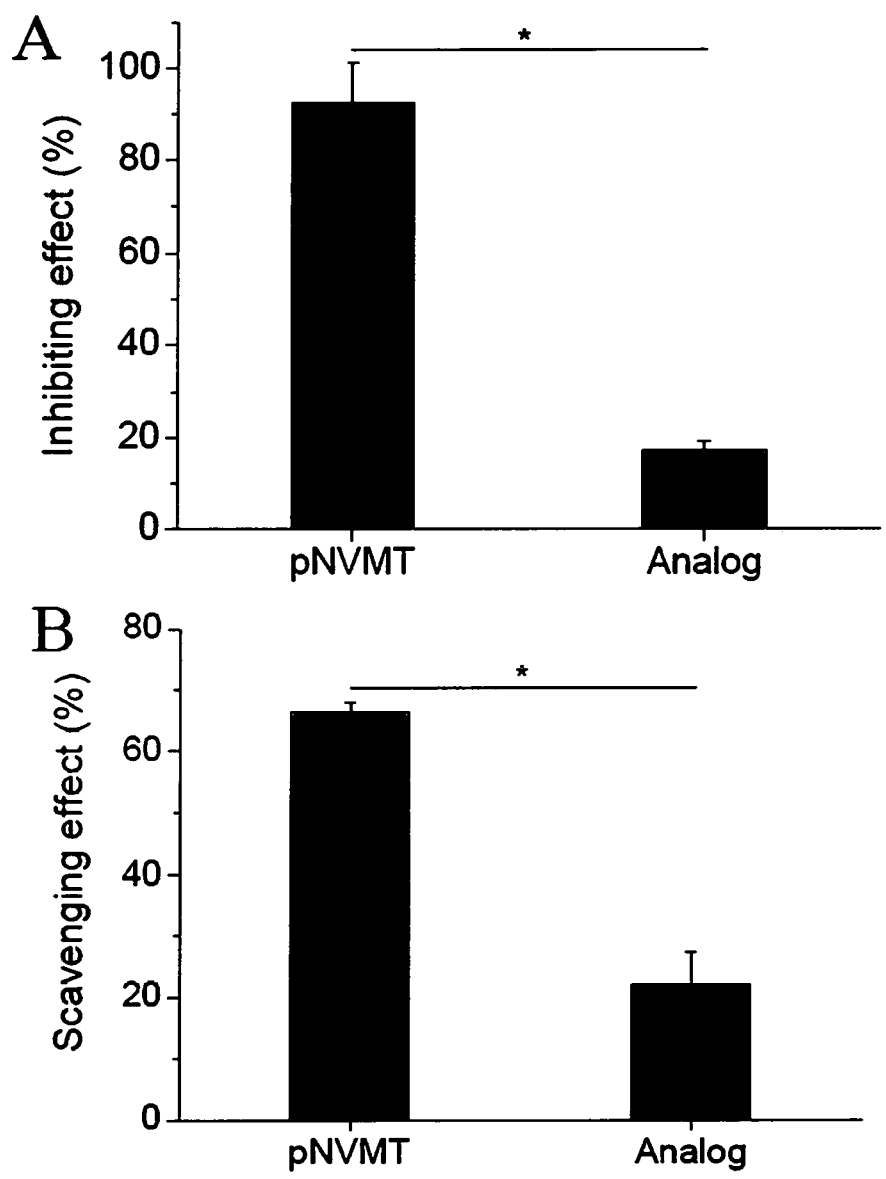
FIG. 3. Scavenging effect of pNVMT in ROS generating chemical reactions. (A) Inhibition of Fenton reaction by pNVMT. (B) Superoxide radical scavenging effect of pNVMT in pyrogallol assay. *Significant differences, $p<0.05$.
Figure 4:
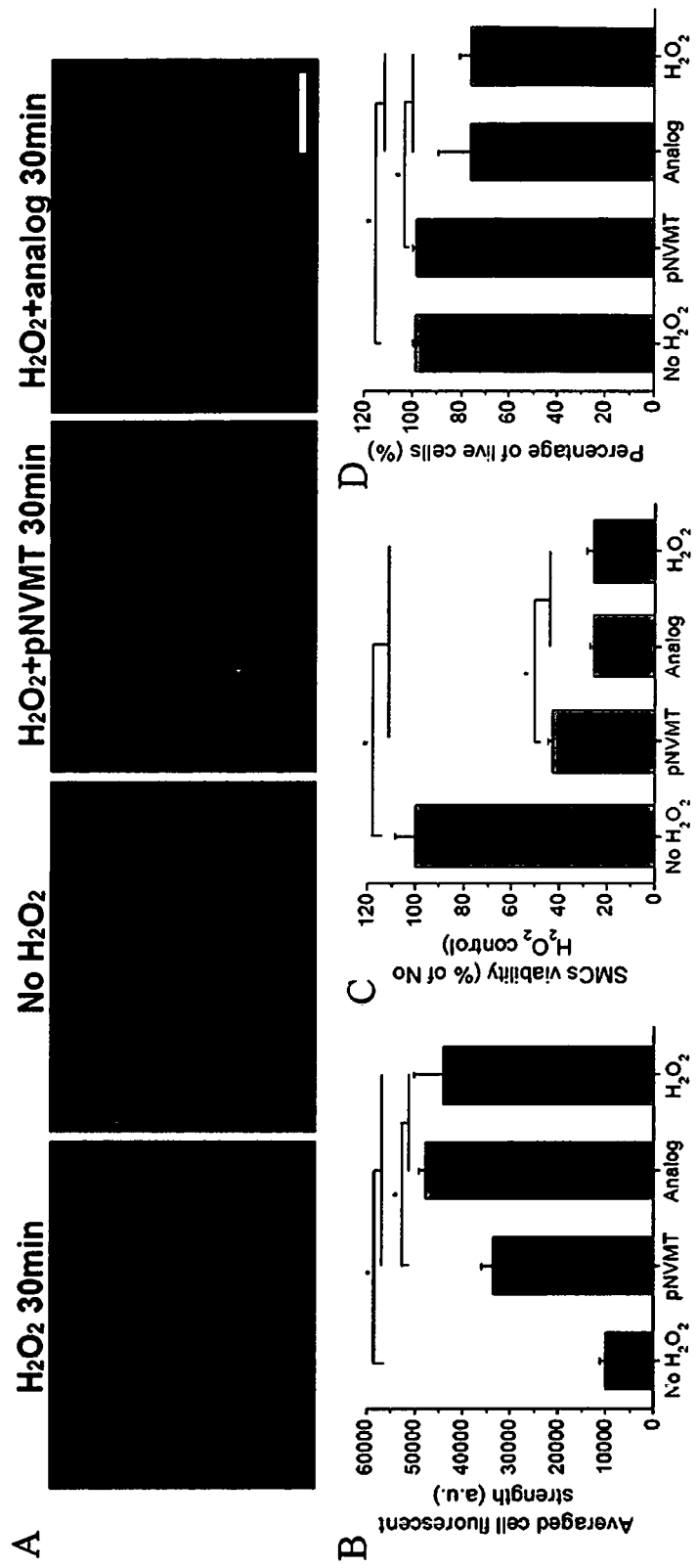
FIG. 4. Antioxidant effect of pNVMT in cell culture. (A, B) Intracellular ROS staining of SMCs treated by 500 μM $H_2O_2$. (C) Viability of $H_2O_2$ treated SMCs determined by MTS assay. (D) Percentage of live cells after $H_2O_2$ treatment determined by live/dead staining. Scale bar=200 μm. *Significant differences, $p<0.05$.

The ROS scavenging effect of pNVMT was first characterized with ROS producing chemical reactions. As shown in FIG. 3A, pNVMT significantly inhibited the Fenton reaction, showing its capability to scavenge hydroxyl radicals, while the analog polymer did not show such an effect. In addition, the superoxide radical scavenging effect of pNVMT was confirmed by the pyrogallol assay (FIG. 3B). In cell culture, adding pNVMT to the culture media protected SMCs from the $H_2O_2$ oxidative stress, which generates a variety of ROS. With the protection of pNVMT, the increase in SMCs intracellular ROS level was significantly less than the negative controls, including the group without protection and the group treated with the analog. As a result, SMC mitochondrial function was less impaired by $H_2O_2$ under the pNVMT protection, leading to a significantly higher survival rate compared to the analog treated group and the non-treated control (FIG. 4). The overall damage caused by the 500 µM $H_2O_2$ treatment with pNVMT scavenging was close to the damage caused by 100 µM $H_2O_2$. Since pNVMT macromolecules did not penetrate the cell membrane of SMCs and gelled extracellularly, the data suggest the potential of pNVMT to lower the ROS concentrations in the extracellular space in vivo, such as in the infarcted myocardium.

Figure 5:
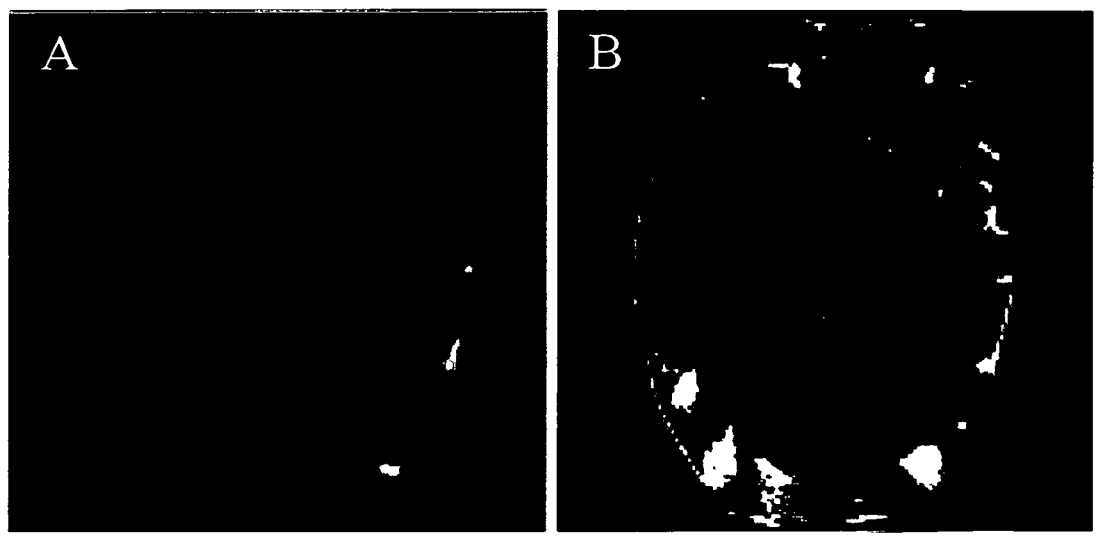
FIG. 5. MRI imaging of pNVMT hydrogel injected rat heart. Hydrogel was injected 30 min after infarction and followed by a 4 h reperfusion. (A) Infarction area under T2 weighted MRI. (B) Injected hydrogel in the left ventricle imaged by T1 weighted MRI.

In myocardial infarction/reperfusion injury, ROS is generated in the infarcted myocardium as a result of circulation restoration, and is followed by the oxidative damage in the infarcted area and the border zone. Therefore, it is important to deliver the ROS scavenging hydrogel into the infarcted area for maximum benefit. TEMPO is widely used as an MRI contrast agent for its nitroxide radical, which adds another advantage to the hydrogel: MRI visibility. The infarction area can be identified under MRI as the dark area in the T2 weighted image (FIG. 5A). pNVMT was injected 30 min after infarction, followed by 4 h of reperfusion. The injected hydrogel can be observed as white areas in the left ventricle (FIG. 5B), which co-localize with the infarction area. This result showed that pNVMT diffused through the tissue, integrated with the myocardium and stayed in the left ventricle during the critical period following reperfusion when ROS are rapidly generated. A detailed study of the in vivo protection effect in the myocardial infarction/reperfusion model is ongoing.

In conclusion, a biodegradable, thermally responsive hydrogel (pNVMT) with ROS scavenging ability was synthesized and its activity confirmed. In an in vitro oxidative environment, pNVMT significantly preserved cell viability. In the rat myocardial infarction/reperfusion model, pNVMT diffused through the infarcted myocardium, integrated with the tissue, and could be visualized under MRI. This thermoresponsive hydrogel has properties desirable for application to tissue beds where cellular oxidative damage is of concern in a variety of disease processes.

In rats, in vivo ischemia by ligating left anterior descending artery for 30 min. was performed. After 30 min ligation, either pNVMT hydrogel, Analog gel, free TEMPO or PBS was directly injected into the infarction area and borderzone. The ligation was then removed following injections to reperfuse the hearts. Hearts were isolated/removed from rats and blood was removed using PBS. Hearts were immediately frozen in liquid nitrogen and stored at −80° C. until the EPR experiments were performed. Heart tissue samples for EPR were prepared by transferring the frozen heart tissue (450-600 mg) into a ceramic mortar pre-chilled with liquid nitrogen. The frozen tissue was maintained at 77 K in liquid nitrogen and broken into small pieces using a pestle. The tissue in liquid nitrogen was then loaded directly in to an EPR finger Dewar containing liquid nitrogen and EPR spectra were recorded.

Figure 6:
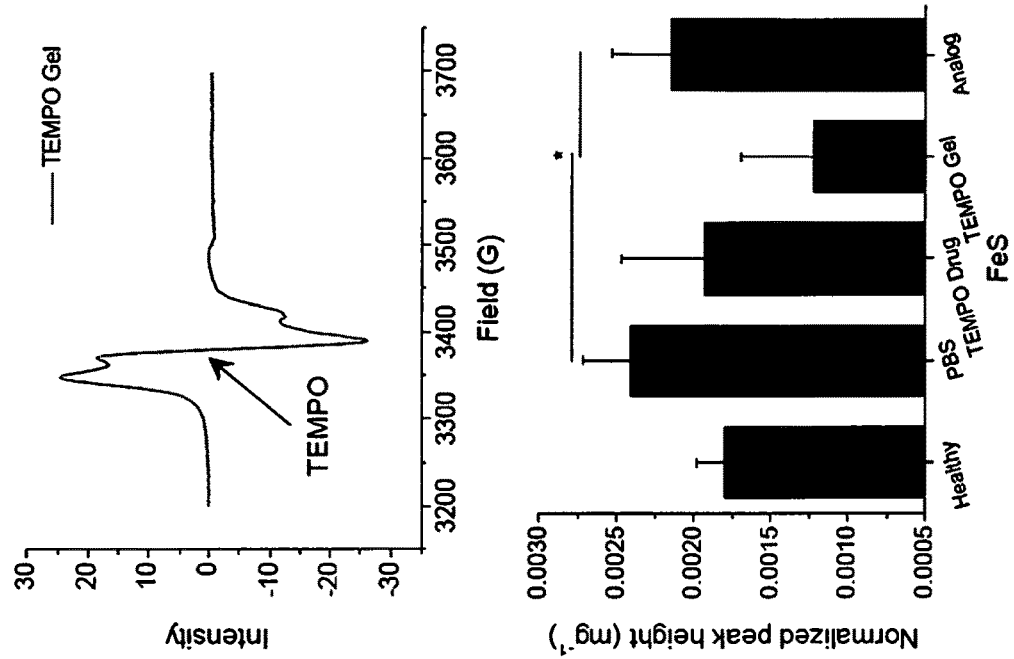
FIG. 6. Top—EPR spectra of rat heart tissue homogenates measured at 77 K. Semiquinone free radicals and Fe(III) from Fe—S centers signals are seen at g=2.01 and g=1.94, respectively. In TEMPO gel treated heart tissues the EPR signals from TEMPO overlap with the semiquinone radical. EPR signal amplitude was normalized against the weight of the heart and expressed as arbitrary units per milligram. Bottom—Normalized EPR signal amplitude of the semiquinone radicals and Fe—S centers (n=4 hearts, *P<0.05). Data are represented as mean±SD. Significant differences (P<0.05) between mean values were determined using One-Way ANOVA. Mitochondrial oxidative stress is decreased in the TEMPO gel treated hearts.
Figure 6:
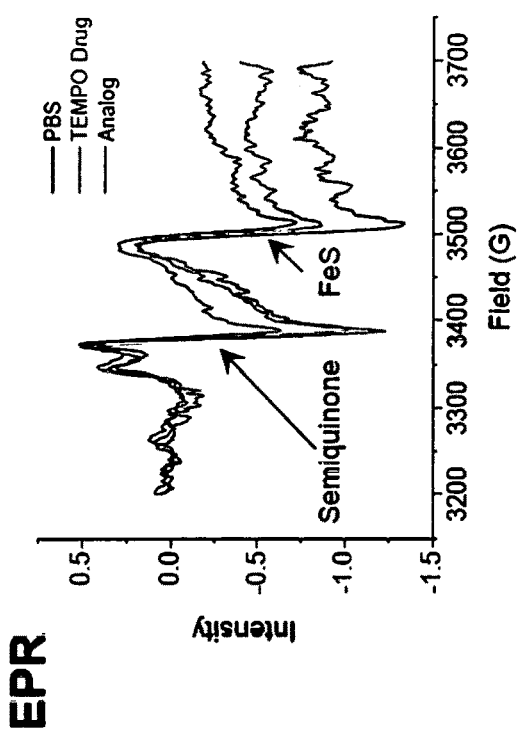
Figure 6:
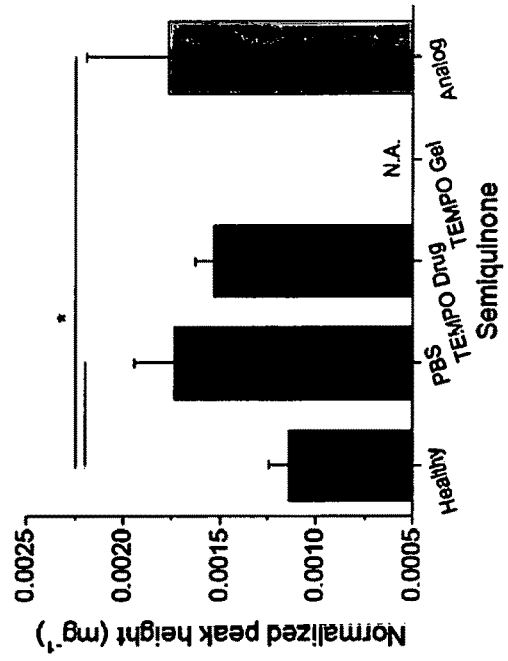

EPR spectra of semiquinone radical and Fe—S centers are shown in FIG. 6 (top). The free radical EPR peak seen at g=2.01 in the heart tissue originates from mitochondrial semiquinone radicals (FIG. 6; top). The peak at g=1.94 corresponds to Fe(III) from mitochondrial iron-sulfur (Fe—S) centers (FIG. 6; top). In TEMPO gel treated heart tissue, the EPR signal from TEMPO radical of the gel overlap with the semiquinone radical signal as shown in FIG. 6 (top right). Both semiquinone radical and Fe(III) signals amplitude from ischemia and reperfusion hearts were higher than the healthy heart (no ischemia and reperfusion). The increased signal amplitude shows that the ischemia and reperfusion increases oxidative stress and mitochondrial dysfunction in the heart. The EPR signal amplitude between PBS and TEMPO drug treated heart was statistically not significant (FIG. 6, bottom). In addition, there was no difference between the PBS and analog treated hearts (FIG. 6, bottom). This shows that the TEMPO drug and analog treatments cannot protect the heart from oxidative stress due to ischemia and reperfusion. Importantly, the EPR signal amplitude from Fe—S centers in TEMPO gel treated heart was decreased and matched with the healthy heart. These EPR results demonstrate that TEMPO gel treatment protects the heart from oxidative damage due to ischemia and reperfusion.

The following numbered clauses are illustrative of various aspects or embodiments of the present invention:

1. A thermal responsive copolymer composition, comprising a hydrocarbyl backbone, and a plurality of pendant pyrrolidone, antioxidant radical, polyester oligomer, and N-alkyl amide groups, the copolymer having a transition temperature between 10° C. and 35° C., or between 15° C. and 30° C., above which temperature, the polymer composition transitions from an aqueous-miscible state to a higher viscosity partially-miscible or immiscible state in an aqueous solution.
2. The composition of clause 1, wherein the polymer composition forms a hydrogel at a temperature above the transition temperature.
3. The composition of clause 1, comprising vinyl pyrrolidone, N alkyl acrylamide, polyester acrylate macromer, and antioxidant acrylate residues.
4. The composition of any one of clauses 1-3, comprising: from 4 mole % to 20 mole % of vinyl pyrrolidone residues, from 70 mole % to 90 mole % of N alkyl acryamide residues, from 4 mole % to 10 mole % of polyester acrylate macromer residues, and from 0.01 mole % to 10 mole % antioxidant acrylate residues.
5. The composition of any one of clauses 1-3, comprising: from 4 mole % to 20 mole %, optionally based on feed ratio, of vinyl pyrrolidone residues, from 70 mole % to 90 mole % of N alkyl acryamide residues, from 4 mole % to 10 mole % of polyester acrylate macromer residues, and from 0.01 mole % to 10 mole % antioxidant acrylate residues.
6. The composition of any one of clauses 1-3, comprising: from 4 mole % to 20 mole % of vinyl pyrrolidone residues, from 70 mole % to 90 mole % of N isopropyl acryamide residues, from 4 mole % to 10 mole % of methacrylate-polylactide macromer residues, and from 0.01 mole % to 10 mole % TEMPO acrylate residues.
7. The composition of clause 2, wherein the polyester acrylate macromer is a methacrylate-polylactide macromer or a hydroxymethacrylate-polytrimethylcarbonate macromer.
8. The composition of any one of clauses 1-6, wherein the polyester oligomer has, on average, two or more polyester linkages.
9. The composition of clause 7, wherein the polyester oligomer comprises, on average, from greater than one to ten lactide or trimethylcarbonate residues.
10. The composition of clause 1, wherein the N-alkyl amide groups are N—$C_{1-4}$ alkyl amide.
11. The composition of clause 1, wherein the N-alkyl amide groups are N-isopropyl amide.
12. The composition of clause 1, wherein the antioxidant radical is a residue chosen from: 4-Hydroxy-TEMPO, 4-carboxy-TEMPO, 4-Cyano-TEMPO, 3β-DOXYL-5α-cholestane (4',4'-dimethylspiro(5α-cholestane-3,2'-oxazolidin)-3'-yloxy), 5-DOXYL-stearic acid (2-(3-carboxypropyl)-4,4-dimethyl-2-tridecyl-3-oxazolidinyloxy), 16-DOXYL-stearic acid (2-(14-carboxytetradecyl)-2-ethyl-4,4-dimethyl-3-oxazolidinyloxy), methyl 5-DOXYL-stearate (2-(4-methoxy-4-oxobutyl)-4,4-dimethyl-2-tridecyl-3-oxazolidinyloxy), 3-(aminomethyl)-PROXYL (3-(aminomethyl)-2,2,5,5-tetramethyl-1-pyrrolidinyloxy), α,γ-bisdiphenylene-β-phenylally, 3-carbamoyl-PROXYL (3-carbamoyl-2,2,5,5-tetramethylpyrrolidin-1-yloxy), 3-carbamoyl-2,2,5,5-tetramethyl-3-pyrrolin-1-oxyl, 3-carboxy-PROXYL (3-(carboxy)-2,2,5,5-tetramethyl-1-pyrrolidinyloxy), 3-cyano-PROXYL (3-cyano-2,2,5,5-tetramethyl-1-pyrrolidinyloxy), Galvinoxyl (2,6-di-tert-butyl-α-(3,5-di-tert-butyl-4-oxo-2,5-cyclo hexadien-1-ylidene)-p-tolyloxy), 4-(1-hydroxy-1-methylethyl)-2,2,5,5-tetramethyl-3-imidazolinium-1-yloxy, 3-(2-iodoacetamido)-PROXYL (3-(2-Iodoacetamido)-2,2,5,5-tetramethyl-1-pyrrolidinyloxy), 3-maleimido-PROXYL (3-maleimido-2,2,5,5-tetramethyl-1-pyrrolidinyloxy), 4-phenacylidene-2,2,5,5-tetramethylimidazolidin-1-yloxy, 4-phenyl-2,2,5,5-tetramethyl-3-imidazolin-1-yloxy, 2,2,5-trimethyl-4-phenyl-3-azahexane-3-nitroxide, and tris(4-bromophenyl)ammoniumyl.
13. The composition of clause 1, wherein the antioxidant radical is a nitroxide antioxidant radical.
14. The composition of clause 13, wherein the nitroxide antioxidant radical is a TEMPO residue.
15. The composition of clause 1, having the structure:

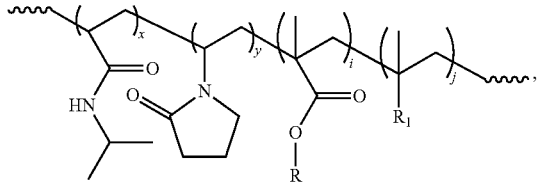

wherein R is a polyester having from 1 to 10 ester linkages, and x, y, I, and j are integers greater than 0, and can be in any order, and $R_1$ is an antioxidant moiety.
16. The composition of clause 1, having the structure:

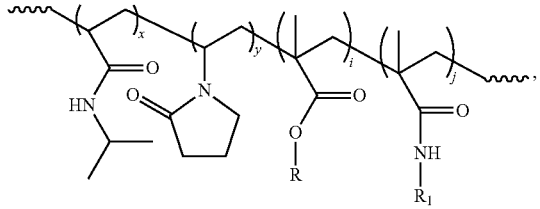

wherein R is a polyester having from 1 to 10 ester linkages, and x, y, I, and j are integers greater than 0, and can be in any order, and $R_1$ is an antioxidant moiety.
17. The composition of clause 16, wherein the antioxidant moiety comprises a nitroxide radical.

18. The composition of clause 16, having the structure:

[chemical structure]

19. The composition of clause 16, having the structure:

[chemical structure]

20. The composition of any one of clauses 1-19, wherein the composition diffuses within tissue when injected in a patient.
21. The composition of any one of clauses 1-19, wherein the composition collapses into a hydrogel mass within tissue when injected in a patient.
22. A method of making an antioxidant polymer composition, comprising:
  polymerizing, using a radical polymerization method, a monomer mixture comprising vinyl pyrrolidone, an acrylate comprising a reactive group, a polyester oligomer acrylate macromer, and an N-alkyl acrylamide; and
  linking an antioxidant radical moiety to the reactive group.
23. The method of clause 22, wherein the reactive group is chosen from: carboxyl (e.g., —C(O)OH) or —(CH$_2$)$_n$CO$_2$Y where n=1-5, Y=any leaving group such as a Cl, alkyl, or aryl), hydroxyl, amine, cyanate, cyano, isocyanate, thiol, epoxide (oxirane), vinyl, allyl, succinimide, oxysuccinimide, azide, alkynyl, maleimide, hydrazide, tetrazine, phosphoramidite, cycloalkyne, and nitrile.
24. The method of clause 22, wherein the reactive groups is an amine-reactive group.
25. The method of clause 22, wherein the antioxidant radical is chosen from: 4-Hydroxy-TEMPO, 4-carboxy-TEMPO, 4-Cyano-TEMPO, 3β-DOXYL-5α-cholestane (4',4'-dimethylspiro(5α-cholestane-3,2'-oxazolidin)-3'-yloxy), 5-DOXYL-stearic acid (2-(3-carboxypropyl)-4,4-dimethyl-2-tridecyl-3-oxazolidinyloxy), 16-DOXYL-stearic acid (2-(14-carboxytetradecyl)-2-ethyl-4,4-dimethyl-3-oxazolidinyloxy), methyl 5-DOXYL-stearate (2-(4-methoxy-4-oxobutyl)-4,4-dimethyl-2-tridecyl-3-oxazolidinyloxy), 3-(aminomethyl)-PROXYL (3-(aminomethyl)-2,2,5,5-tetramethyl-1-pyrrolidinyloxy), α,γ-bisdiphenylene-β-phenylally, 3-carbamoyl-PROXYL (3-carbamoyl-2,2,5,5-tetramethylpyrrolidin-1-yloxy), 3-carbamoyl-2,2,5,5-tetramethyl-3-pyrrolin-1-oxyl, 3-carboxy-PROXYL (3-(carboxy)-2,2,5,5-tetramethyl-1-pyrrolidinyloxy), 3-cyano-PROXYL (3-cyano-2,2,5,5-tetramethyl-1-pyrrolidinyloxy), Galvinoxyl (2,6-di-tert-butyl-α-(3,5-di-tert-butyl-4-oxo-2,5-cyclohexadien-1-ylidene)-p-tolyloxy), 4-(1-hydroxy-1-methylethyl)-2,2,5,5-tetramethyl-3-imidazolinium-1-yloxy, 3-(2-iodoacetamido)-PROXYL (3-(2-Iodoacetamido)-2,2,5,5-tetramethyl-1-pyrrolidinyloxy), 3-maleimido-PROXYL (3-maleimido-2,2,5,5-tetramethyl-1-pyrrolidinyloxy), 4-phenacylidene-2,2,5,5-tetramethylimidazolidin-1-yloxy, 4-phenyl-2,2,5,5-tetramethyl-3-imidazolin-1-yloxy, 2,2,5-trimethyl-4-phenyl-3-azahexane-3-nitroxide, and tris(4-bromophenyl)ammoniumyl.
26. The method of clause 22, wherein the antioxidant radical is a nitroxide antioxidant radical.
27. The method of clause 26, wherein the nitroxide antioxidant radical is a TEMPO residue.
28. The method of any one of clauses 22-27, wherein the polyester acrylate macromer is a methacrylate-polylactide macromer or a hydroxymethacrylate-polytrimethylcarbonate macromer.
29. The method of any one of clauses 22-28, wherein the polyester of the polyester acrylate macromer has, on average, two or more polyester linkages.
30. The method of clause 29, wherein the polyester oligomer comprises, on average, from greater than one to ten lactide or trimethylcarbonate residues.
31. The method of any one of clauses 22-30, wherein the N-alkyl amide groups are N—C$_{1-4}$ alkyl amide.
32. The method of clause 31, wherein the N-alkyl amide groups are n-isopropyl amide.
33. The method of clause 29, comprising:
  polymerizing, using a radical polymerization method, a mixture of monomers comprising vinyl pyrrolidone, methacryloxy N-hydroxysuccinimide, a methacrylate-polylactide macromer, and n-isopropyl acrylamide; and
  linking 4-amino TEMPO to the N-hydroxysuccinimide.
34. A method of treating ischemia or an ischemia reperfusion injury in a patient, comprising administering to a patient at a site of ischemia a composition of any one of clauses 1-21.
35. The method of clause 34, wherein the ischemia or ischemia reperfusion injury is a cardiac infarct, a chronic wound, a diabetic foot ulcer, CNS tissue, or transplanted tissue.
36. The method of clause 34, wherein the composition has sufficient hydrophilicity, such as sufficient pyrrolidone content, to diffuse into the ischemic or reperfused tissue.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

What is claimed is:
1. A thermal responsive, biodegradable copolymer composition, comprising n-isopropylacrylamide (NIPAAm) residues, vinyl pyrrolidone residues, methacrylate-polylactide (MAPLA) residues, and methacrylate-TEMPO (MATEMPO), the (MATEMPO) bound to one or more of the MAPLA residues through an amide bond, the copolymer having a transition temperature between 10° C. and 35° C., or between 15° C. and 30° C., above which temperature, the polymer composition transitions from an aqueous-miscible state to a hydrogel having a higher viscosity, partially-miscible or immiscible state in an aqueous solution.

2. The composition of claim 1, comprising: from 4 mole % to 20 mole % of vinyl pyrrolidone residues, from 70 mole % to 90 mole % of NIPAAm residues, from 4 mole % to 10 mole % of MAPLA residues, and from 0.01 mole % to 10 mole % MATEMPO residues.

3. The composition of claim 1, wherein the composition is able to diffuse within tissue when injected in a patient.

* * * * *